United States Patent [19]

Furuya et al.

[11] Patent Number: 4,978,651
[45] Date of Patent: Dec. 18, 1990

[54] PHENOLIC COMPOUNDS AND RECORDING MATERIAL COMPRISING THE SAME

[75] Inventors: Hiromi Furuya, Shimizu; Kunio Hayakawa, Gotemba, both of Japan

[73] Assignee: Ricoh Company, Ltd., Tokyo, Japan

[21] Appl. No.: 369,021

[22] Filed: Jun. 21, 1989

[30] Foreign Application Priority Data

Jun. 23, 1988 [JP] Japan .................................. 63-156403
Sep. 30, 1988 [JP] Japan .................................. 63-247040

[51] Int. Cl.$^5$ ......................... B41M 5/16; B41M 5/18
[52] U.S. Cl. .................................. 503/216; 427/150; 503/225
[58] Field of Search ................................. 427/150-152; 503/216, 225

[56] References Cited

U.S. PATENT DOCUMENTS 4,502,065 2/1985 Taniguchi et al. .................. 503/216

Primary Examiner—Bruce H. Hess
Attorney, Agent, or Firm—Oblon, Spivak, McClelland, Maier & Neustadt

[57] ABSTRACT

A phenolic compound having formula (I):

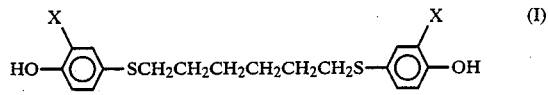

wherein X represents a chlorine atom or a methyl group, and a recording material comprising a coloress or light-colored leuco dye and the above phenolic compound serving as a color developer for the leuco dye are disclosed.

3 Claims, No Drawings

PHENOLIC COMPOUNDS AND RECORDING MATERIAL COMPRISING THE SAME

BACKGROUND OF THE INVENTION

1. Field of the Invention

This invention relates to novel phenolic compounds, and a recording material comprising any of the same as a color developing agent.

2. Discussion of Background

Hitherto, various recording materials utilizing a color-developing reaction between colorless or light-colored leuco dyes and color-developing agents, which is initiated with the application of heat or pressure, have been proposed.

Developing and fixing processes are not necessary when images are transferred through a thermosensitive recording material which is one of the above recording materials. Therefore, the thermosensitive recording material does not require a complicated apparatus, and images can be transferred to a recording sheet speedily without generating noise. Furthermore, the price of the thermosensitive recording material is relatively inexpensive.

Because of the above advantages, the thermosensitive recording material is employable in various fields, for instance, for use with terminal printers for computers, facsimile apparatus, automatic ticket vending apparatus, label printing machines, and recorders for various apparatus and instruments.

In general, the thermosensitive recording material comprises as a color-producing dye a colorless or light-colored leuco dye having an atomic group of lactone, lactam or spiropyran, and as a color developing agent such as an organic acidic material or phenolic material. When the above recording material is employed, images can be obtained with high density without coloring the background of the recording sheet, so that it enjoys general popurality.

With the recent increase of the demand for a recording method using the thermosensitive recording material, the requirement for recording at higher speed is getting greater. In order to meet such a requirement, not only a recorder operable at high speed but also a recording material usable with a high-speed recorder is now being developed.

In order to attain high-speed recording, various manners for improving the sensitivity of the thermosensitive recording material have been proposed.

For instance, some high-sensitive color-developing agents for use in the recording material, such as p-hydroxyl benzoic ester as disclosed in Japanese Laid-Open Patent Application No. 56-144193, hydroxyl naphthoic ester as disclosed in Japanese Laid-Open Patent Application No. 59-22793, and phenolic compounds having a thioether group as disclosed in Japanese Laid-Open Patent Application Nos. 59-52694 and 59-73993, have been proposed.

The sensitivity of the recording material can also be improved by incorporating various thermofusible materials therein. As such thermofusible materials, naphthol derivatives and benzyl biphenyls have been proposed in Japanese Laid-Open Patent Application Nos. 58-87094 and 60-82382, respectively.

However, the recording material comprising the above color-developing agent or thermofusible material is not yet satisfactory when the color-developing sensitivity, the whiteness of the background, and the preservability of the transferred images are taken into consideration.

Japanese Laid-Open Patent Application No. 62-181182 discloses a recording material comprising as a color-developing agent a hydroxyphenyl thiol derivative capable of being substituted, and as a thermofusible material an aryl compound. However, this recording material is decolored or becomes white when it is brought into contact with water due to the presence of the hydroxyphenyl thiol derivative, and an increased amount of scum is deposited to a thermal head when images are transferred through the recording material due to the presence of the aryl compound. Furthermore, no specific examples of the susbstituted hydroxyphenyl thiol derivatives ar disclosed in this application.

SUMMARY OF THE INVENTION

Accordingly, an object of the present invention is to provide novel phenolic compounds which are suitable as a color-developing agent for use in a recording material.

Another object of the present invention is to provide a recording material comprising any of the phenolic compounds as a color-developing agent, which are excellent in color-developing sensitivity and suitable for high-speed recording, has high preservability, and gives high whiteness to the background.

The first object of the invention can be attained by the following phenolic compounds:

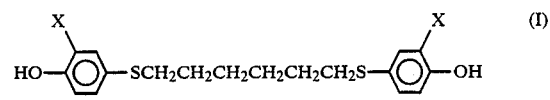

wherein X represents a chlorine atom or a methyl group.

The second object of the invention can be attained by a recording material comprising a colorless or light-colored leuco dye and any of the above phenolic compounds serving as a color developer capable of inducing color in the leuco dye upon reacting with the leuco dye.

DETAILED DESCRIPTION OF THE PREFERRED EMBODIMENTS

The phenolic compounds having the above formula (I) according to the present invention can be readily synthesized in accordance with the following reaction scheme.

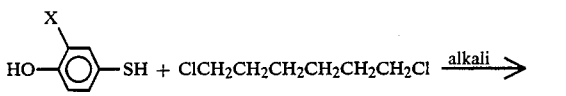

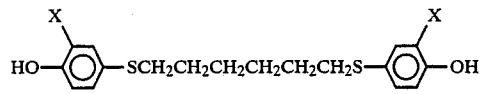

wherein X represents a chlorine atom or a methyl group. Specifically, the phenolic compounds are:

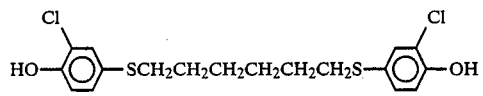

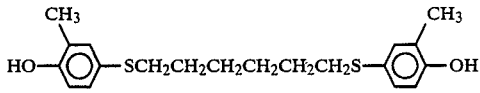

The above reaction proceeds in a solvent at any temperatures. Preferable examples of such a solvent include methanol, ethanol, toluene, benzene, dimethyl sulfoxide, N,N-dimethyl formamide, tetrahydrofuran, 1,4-dioxane, and water. These solvents can be used singly or in combination. As the alkaline substance to be added to the reaction system, sodium hydroxide, potassium hydroxide, potassium carbonate, triethyl amine, and pyridine can be employed.

The conventional leuco dyes can be used in the recording material of the present invention along with any of the phenolic compounds. Preferable examples of such leuco dyes include triphenyl methane type leuco compounds, fluorane type leuco compounds, phenothiadine leuco compounds, Auramine type leuco compounds, spiropyran type leuco compounds, and indolinophthalide type leuco compounds. The above leuco dyes are used singly or in combination. Specific examples of the leuco dyes are as follows:
3,3-bis(p-dimethylaminophenyl)phthalide,
3,3-bis(p-dimethylaminophenyl)-6-dimethylaminophthalide (=Crystal Violet lactone),
3,3-bis(p-dimethylaminophenyl)-6-diethylaminophtalide,
3,3-bis(p-dimethylaminophenyl)-6-chlorophthalide,
3,3-bis(p-dibutylaminophenyl)phthalide,
3,3-cyclohexylamino-6-chlorofluoran,
3,3-dimethylamino-5,7-dimethylfluoran,
3-(N-methyl-N-isobutylamino)-6-methyl-7-anilinofluoran,
3-(N-ethyl-N-isoamylamino)-6-methyl-7-anilinofluoran,
3-diethylamino-7-chlorofluoran,
3-diethylamino-7-methylfluoran,
3-diethylamino-7,8-benzfluoran,
3-diethylamino-6-methyl-7-chlorofluoran,
3-(N-p-tolyl-N-ethylamino)-6-methyl-7-anilinofluoran,
3-pyridino-6-methyl-7-anilinofluoran,
2-{N-(3'-trifluoromethylphenyl)amino}-6-diethylaminofluoran,
2-{3,6-bis(diethylamino)-9-(o-chloroanilino)xanthyllactam benzoate),
3-diethylamino-6-methyl-7-(m-trichloromethylanilino)fluoran,
3-diethylamino-7-(o-chloroanilino)fluoran,
3-dibutylamino-7-(o-chloroanilino)fluoran,
3-N-methyl-N-amylamino-6-methyl-7-anilinofluoran,
3-N-methyl-N-cyclohexylamino-6-methyl-7-anilinofluoran,
3-diethylamino-6-methyl-7-anilinofluoran,
3-diethylamino-6-methyl-7-(2',4'-dimethylanilino)fluoran,
3-(N,N-diethylamino)-5-methyl-7-(N,N-dibenzylamino)fluoran,
benzoyl leuco Methylene Blue,
6'-chloro-8'-methoxy-benzoindolino-spiropyran,
6'-bromo-3'-methoxy-benzoindolino-spiropyran,
3-(2'-hydroxy-4'-dimethylaminophenyl)-3-(2'-methoxy-5'-chlorophenyl)phthalide,
3-(2'-hydroxy-4'-dimethylaminophenyl)-3-(2'-methoxy-5'-nitrophenyl)phthalide,
3-(2'-hydroxy-4'-diethylaminophenyl)-3-(2'-methoxy-5'-methylphenyl)phthalide,
3-(2'-methoxy-4'-dimethylaminophenyl)-3-(2'-hydroxy-4'-chloro-5'-methylphenyl) phthalide,
3-morpholino-7-(N-propyl-trifluoromethylanilino)fluoran,
3-pyrrolidino-7-trifluoromethylanilinofluoran,
3-diethylamino-5-chloro-7-(N-benzyl-trifluoromethylanilino)fluoran,
3-pyrrolidino-7-(di-p-chlorophenyl)methylaminofluoran,
3-diethylamino-5-chloro-7-(α-phenylethylamino)fluoran,
3-(N-ethyl-p-toluidino)-7-(α-phenylethylamino)fluoran,
3-diethylamino-7-(o-methoxycarbonylphenylamino)fluoran,
3-diethylamino-5-methyl-7-(α-phenylethylamino)fluoran,
3-diethylamino-7-piperidinofluoran,
2-chloro-3-(N-methyltoluidino)-7-(p-n-butylanilino)fluoran,
3-(N-methyl-N-isopropylamino)-6-methyl-7-anilinofluoran,
3-dibutylamino-6-methyl-7-anilinofluoran,
3,6-bis(dimethylamino)fluorene spiro(9,3')-6'-dimethylaminophthalide,
3-(N-benzyl-N-cyclohexylamino)-5,6-benzo-7-α-naphthylamino-4'-bromofluoran,
3-diethylamino-6-chloro-7-anilinofluoran,
3-N-ethyl-N-(2-ethoxypropyl)amino-6-methyl-7-anilinofluoran,
3-N-ethyl-N-tetrahydrofurfurylamino-6-methyl-7-anilinofluoran,
3-diethylamino-6-methyl-7-mesidino-4',5'-benzofluoran,
3-(p-dimethylaminophenyl)-3-{1,1-bis(p-dimethylaminophenyl)ethylene-2-il}phthalide,
3-(p-dimethylaminophenyl)-3-{1,1-bis(p-dimethylaminophenyl)ethylene-2-il}-6-dimethylaminophthalide,
3-(p-dimethylaminophenyl)-3-(1-p-dimethylaminophenylethylene-2-il)phthalide,
3(p-dimethylaminophenyl)-3-(1-p-dimethylaminophenyl-1-p-chlorophenylethylene-2-il)-6-dimethylaminophtha lide,
3-(4'-dimethylamino-2'-methoxy)-3-(1''-p-dimethylaminophenyl-1''-p-chlorophenyl-1'',3''-butadiene-4''-il)benzophthalide,
3-(4'-dimethylamino-2'-benzyloxy)-3-(1''-p-dimethylaminophenyl-1''-phenyl-1'',3''butadiene-4''-il)benzophthalide,
3-dimethylamino-6-dimethylamino-fluorene-9-spiro-3'-(6'-dimethylamino)phthalide,
3,3-bis{2-(p-dimethylaminophenyl)-2-(p-methoxyphenyl)ethenyl}-4,5,6,7-tetrachlorophthalide,
3-bis{1,1-bis(4-pyrrolidinophenyl)ethylene-2-il}-5,6-dichloro-4,7-dibromophthalide, and
bis(p-dimethylaminostylyl)-1-naphthalenesulfonylmethane.

In the recording material of the present invention, various electron accepting compounds such as phenolic compounds, thiophenolic compounds, thiourea derivatives, organic acids and metal salts thereof may be used together with the phenolic compound having formula (I).

Specific examples of such electron accepting compounds are as follows:
4,4'-isopropylidene bisphenol,
4,4'-isopropylidene bis(o-methylphenol),
4,4'-sec-butylidene bisphenol, 4,4'-isopropylidene bis(2-tert-butylphenol),
4,4'-cyclohexylidene diphenol,
4'-isopropylidene bis(2-chlorophenol),
2,2'-methylene bis(4-methyl-6-tert-butylphenol),
2,2'-methylene bis(4-ethyl-6-tert-butylphenol),
4,4'-butylidene bis(6-tert-butyl-2-methylphenol),
1,1,3-tris(2-methyl-4-hydroxy-5-tert-butylphenyl)butane,
1,1,3-tris(2-methyl-4-hydroxy-5-cyclohexylphenyl)butane,
4,4'-thiobis(6-tert-butyl-2-methylphenol),
4,4'-diphenolsulfone,
4-isopropoxy-4'-hydroxydiphenylsulfone,
4-benzyloxy-4'-hydroxydiphenylsulfone,
4,4'-diphenolsulfoxide,
isopropyl p-hydroxybenzoate,
benzyl p-hydroxybenzoate,
benzyl protocatechuate,
stearyl gallate,
lauryl gallate,
octyl gallate,
1,3-bis(4-hydroxyphenylthio)propane,
1,3-bis(4-hydroxyphenylthio)-2-hydroxypropane,
N,N'-diphenylthiourea,
N,N'-di(m-chlorophenyl)thiourea,
salicylanilide,
5-chloro-salicylanilide,
bis-(4-hydroxyphenyl)acetic methylacetate,
bis-(4-hydroxyphenyl)acetic benzylacetate,
1,3-bis(4-hydroxycumyl)benzene,
1,4-bis(4-hydroxycumyl)benzene,
2,4'-diphenolsulfone,
2,2'-diallyl-4,4'-diphenolsulfone,
3,4-dihydroxy-4'-methyldiphenylsulfone,
zinc 1-acetyloxy-2-naphthoate,
zinc 2-acetyloxy-1-naphthoate,
zinc 2-acetyloxy-3-naphtoate,
α,α-bis(4-hydroxyphenyl)-α-methyltoluene,
antipyrine complexes of zinc thiocyanate,
tetrabromobisphenol A, and
tetrabromobisphenol S.

The recording material according to the present invention can be prepared by applying any of the leuco dyes and any of the phenolic compounds serving as a color developer, together with a binder agent, to a substrate.

As the binder agent, the following compounds, which have conventionally been used as a binder, can be used: polyvinyl alcohol; starch and derivatives thereof; cellulose derivatives such as methoxycellulose, hydroxyethylcellulose, carboxymethyl cellulose, methyl cellulose and ethyl cellulose; water-soluble polymers such as sodium polyacrylate, polyvinyl pyrrolidone, a copolymer of acrylamide and acrylate, a copolymer of acrylamide, acrylate and methacrylate, alkaline salts of a copolymer of styrene and maleic anhydride, alkaline salts of a copolymer of isobutylene and maleic anhydride, polyacrylamide, sodium alginate, gelatin and casein; emulsions such as of polyvinyl acetate, polyurethane, polyacrylate, polymethacrylate, a copolymer of vinylchloride and vinyl acetate and a copolymer of ethylene and vinylacetate; and latices such as of a copolymer of styrene and butadiene and a copolymer of styrene, butadiene and acrylate.

When a thermosensitive recording material is prepared in accordance with the present invention, various thermofusible materials may be employed so as to improve the thermosensitivity. Examples of such thermofusible materials include fatty acids such as stearic acid and behenic acid; fatty acid amides such as stearic acid amide and palmitic acid amide; metal salts of fatty acid such as zinc stearate, aluminum stearate, calcium stearate, zinc palmitate, zinc behenate; and organic compounds such as p-benzylbiphenyl methane, p-benzyltertphenyl methane, p-benzyltriphenyl methane, p-benzyloxy benzylbenzoate, β-benzyloxy naphtharene, β-naphthoic acid phenyl ester, 1-hydroxy-2-naphthoic acid phenyl ester, 1-hydroxy-2-naphthoic acid methyl ester, diphenyl carbonate, terephthalic acid dibenzyl ester, terephthalic acid dimethyl ester, 1,4-dimethoxynaphtharene, 1,4-diethoxynaphtharene, 1,4-dibenzyl oxynaphtharene, 1,2-bis(phenoxy)ethane, 1,2-bis(3-methylphenoxy)ethane, 1,2-bis(4-methylphenoxy)ethane, 1,4-bis(phenoxy)butane, 1,4-bis(phenoxy)-2-butene, 1,2-bis(4-methoxyphenylthio)ethane, dibenzoyl methane, 1,4-bis(phenylthio)butane, 1,4-bis(phenylthio)-2-butene, 1,2-bis(4-methoxyphenylthio)ethane, 1,3-bis(2-vinyloxyethoxy)benzene, 1,3-bis(2-vinyloxyethoxy)benzene, 1,4-bis(2-vinyloxyethoxy)benzene, p-(2-vinyloxyethoxy)biphenyl, p-aryloxybiphenyl, p-propargyl oxybiphenyl, dibenzoyl oxymethane, 1,3-dibenzoyl oxypropane, dibenzyl disulfide, 1,1-diphenyl ethanol, 1,1-diphenylpropanol, p-(benzyloxy)benzylalcohol, 1,3-diphenoxy-2-propanol, N-octadecyl carbamoyl-p-methoxycarbonyl benzene, and N-octadecyl carbamoyl benzene.

Auxiliary components such as fillers and surface active agents which are commonly used for the conventional thermosensitive recording materials may be employed, if necessary, in the thermosensitive recording material according to the present invention.

As the fillers, fine powder of inorganic materials such as of calcium carbonate, silica, zinc oxide, titanium oxide, aluminum hydroxide, zinc hydroxide, barium sulfate, clay, talc, surface-treated calcium, and surface-treated silica; and fine powder of organic materials such as of urea-formalin resin, a copolymer of styrene and methacylic acid, and polystyrene resin can be used.

A pressure-sensitive recording material is also readily obtainable, in accordance with the conventionally known method, by using the phenolic compounds of the present invention as a color developer.

The recording material comprising, as a color developer, the phenolic compounds of the present invention are excellent in the color density and coloring sensitivity. Moreover, images transferred through the recording material have high preservability, especially high resistance to water, and high whiteness of the background is ensured.

Other features of this invention will become apparent in the course of the following description of exemplary embodiments, which are given for illustration of the invention and are not intended to be limiting thereof.

SYNTHESIS EXAMPLE 1

3.2 g of sodium hydroxide and 12.8 g of 2-chloro-4-mercaptophenol were dissolved in 100 ml of methanol at room temperature. 9.3 g of 1,6-dibromohexane was added dropwise to the above mixture, and then the resultant was heated for reaction for three hours under reflux with methanol. After the reaction was completed, the reaction mixture was cooled to room temperature, and precipitated sodium bromide was removed. Methanol contained in the mixture was distilled off under reduced pressure, and the remaining viscous material was placed in 1 l of water, thereby obtaining crude crystals.

The crystals were washed with water twice, followed by recrystalization from a mixed solvent of toluene and ethylacetate, whereby 13.9 g of white crystals of 1,6-bis(3-chloro-4-hydroxyphenylthio)hexane having a melting point of 99° to 103° C. was obtained.

SYNTHESIS EXAMPLE 2

Synthesis Example 1 was repeated except that 12.8 g of 2-chloro-40 mercaptophenol used in Synthesis Example 1 was replaced with 11.2 g of 2methyl-4-mercaptophenol, whereby 11.7 g of white crystals of 1,6-bis (3-methyl-4-hydroxyphenylthio)hexane having a melting point of 86° to 89° C. was obtained.

EXAMPLES 1 AND 2, AND COMPARATIVE EXAMPLES 1 TO 4

Liquids [A], [B] and [C] each having the following formulation were prepared in such a manner that the components of each liquid were placed in a ceramic ball mill and pulverized for two days.

|  | parts by weight |
|---|---|
| Formulation of Liquid [A] | |
| 3-(N-methyl-N-cyclohexylamino-6-methyl-7-anilinofluoran | 20 |
| 10% Aqueous solution of polyvinyl alcohol | 20 |
| Water | 60 |
| Formulation of Liquid [B] | |
| Phenolic compound shown in Table 1 | 20 |
| 10% Aqueous solution of polyvinyl alcohol | 20 |
| Water | 60 |
| Formulation of Liquid [C] | |
| Calcium carbonate | 20 |
| 5% Aqueous solution of methyl cellulose | 20 |
| Water | 60 |

A liquid for forming a thermosensitive color-developing layer was prepared by blending 10 parts by weight of liquid [A], 30 parts by weight of liquid [B] and 30 parts by weight of liquid [C]. The thus prepared liquid was applied to a sheet of high quality paper having a weight of 50 g/m² and dried, thereby forming a thermosensitive coloring layer containing the dye in an amount of 0.5 g/m². The layer was calendered to obtain a thermosensitive recording material having a surface-smoothness of 500 to 600 seconds, whereby thermosensitive recording materials No. 1 and No. 2 according to the present invention and comparative thermosensitive recording materials No. 1 to No. 4 were prepared.

The thus prepared thermosensitive recording materials No. 1 and No. 2 according to the present invention and the comparative thermosensitive recording materials No. 1 through No. 4 were subjected to thermal printing test by use of a thermal printing test apparatus including a thermal head of a thin film type (made by Matsushita Electronic Components Co., Ltd.) under the conditions that the voltage applied to the head was 13.3 V, with the pulse width applied thereto changed to 3 steps of 0.2 msec, 0.3 msec, and 0.4 msec. The density of the developed images was measured by Macbeth densitometer RD-514 with a filter W-106.

The above image-bearing recording materials were allowed to stand at room temperature for one week. Thereafter, the images were visually inspected to see whether a white powder was formed or not in the image areas.

In the thermosensitive recording materials No.1 and No. 2 according to the present invention and the comparative recording materials No. 1 through No. 4, images were developed by a block heated to 130° C., and the image-bearing thermosensitive recording materials were immersed in city water. The image densities of the images before and after the above immersing in water were measured.

The results are shown in Table 1.

TABLE 1

|  | Phenolic Compounds | Density of Background | Developed Image Density | | | White Powder on Developed Images | Water-Resistance of Developed Images | |
|---|---|---|---|---|---|---|---|---|
|  |  |  | 0.2 ms | 0.3 ms | 0.4 ms |  | Before test | After test |
| Example 1 | 1,6-bis(3-chloro-4-hydroxyphenylthio)hexane | 0.09 | 0.22 | 0.78 | 1.28 | Not formed | 1.38 | 1.19 |
| Example 2 | 1,6-bis(3-methyl-4-hydroxyphenylthio)hexane | 0.09 | 0.40 | 1.07 | 1.30 | Not formed | 1.37 | 1.17 |
| Comparative Example 1 | 1,7-bis(4-hydroxyphenylthio)-3,5-dioxaheptane | 0.08 | 0.20 | 0.65 | 1.27 | Not formed | 1.39 | 0.88 |
| Comparative Example 2 | 1,5-bis(4-hydroxyphenythio)-3-oxapentane | 0.09 | 0.38 | 1.04 | 1.31 | Not formed | 1.39 | 0.91 |
| Comparative Example 3 | 4,4'-isopropylidene diphenol | 0.10 | 0.11 | 0.20 | 0.51 | Not formed | 1.29 | 0.90 |
| Comparative Example 4 | p-hydroxybenzylbenzoate | 0.10 | 0.18 | 0.61 | 1.23 | Formed | 1.38 | 0.74 |

The results shown in Table 1 demonstrate that the thermosensitive recording materials of the present invention have high sensitivity, and no white powder is formed in the developed images. Furthermore, the developed images are highly resistant to water.

What is claimed is:

1. A recording material comprising a colorless or light-colored leuco dye, and a phenolic compound having formula (I) capable of inducing color formation in said colorless or light-colored leuco dye upon reacting therewith:

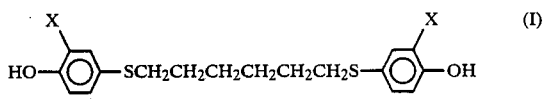

wherein X represents a chlorine atom or a methyl group.

2. The recording material as claimed in claim 1, wherein said phenolic compound has a formula:

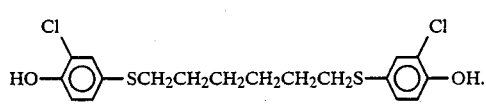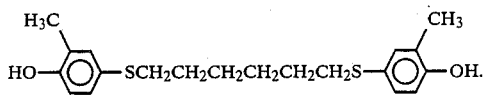
3. The recording material as claimed in claim 1, wherein said phenolic compound has a formula:
* * * * *